United States Patent

Menzi et al.

Patent Number: 6,056,949
Date of Patent: May 2, 2000

[54] AROMATIC GRANULATED MATERIAL

[75] Inventors: Heini Menzi, Gossau; Matthias Perren, Brugg; Rudolf Ringgenberg, Rümlang, all of Switzerland

[73] Assignee: Givaudan Roure (International) SA, Switzerland

[21] Appl. No.: 09/051,343

[22] PCT Filed: Oct. 23, 1996

[86] PCT No.: PCT/CH96/00373

§ 371 Date: Apr. 6, 1998

§ 102(e) Date: Apr. 6, 1998

[87] PCT Pub. No.: WO97/16078

PCT Pub. Date: May 9, 1997

[30] Foreign Application Priority Data

Oct. 27, 1995 [CH] Switzerland .............................. 3037/95
Oct. 15, 1996 [CH] Switzerland .............................. 2518/96

[51] Int. Cl.[7] ........................................................ A61K 9/14
[52] U.S. Cl. .................... 424/76.1; 424/76.2; 424/76.21; 424/76.4; 424/461; 424/469; 427/213.31; 427/213.32
[58] Field of Search ...................... 424/489, 464, 424/490, 465; 427/213.31, 213.32

[56] References Cited

U.S. PATENT DOCUMENTS

3,903,295  9/1975  Palmer .
4,542,043  9/1985  Abe et al. .

FOREIGN PATENT DOCUMENTS

0070719  7/1982  European Pat. Off. .
0252407  6/1987  European Pat. Off. .

OTHER PUBLICATIONS

Food Marketing & Technology, Menzi, H., "An Innovation in Flavour Technnology", (Jun. 1996).

The World of Ingredients, O'Carroll, P., vol. 3–4, (1995) pp. 36–37, "Encapsulation, Inter Alia Granuseal".

*Primary Examiner*—Thurman K. Page
*Assistant Examiner*—William E. Benston, Jr.
*Attorney, Agent, or Firm*—Wood, Herron & Evans, L.L.P.

[57] ABSTRACT

The present invention relates to a process for the preparation of spherical or substantially spherical, practically dust-free aromatic and odoriferous granulated material which is free-flowing, mechanically stable and has a narrow grain-size distribution.

24 Claims, 1 Drawing Sheet

AROMATIC GRANULATED MATERIAL

BACKGROUND OF THE INVENTION

The present invention is concerned with a process for the manufacture of spherical or essentially spherical, practically dust-free, free-flowing, mechanically stable flavorant and odorant granulates having a narrow particle size distribution.

Under "spherical" there is to be understood in the present case a bead-like or an essentially bead-like material upon visual observation with the naked eye.

Flavorant granulates are known. EP 0070719 describes the manufacture of flavorant granulates which are manufactured in a conventional fluidized bed formed simply by the whirling-up of air. These products have, however, the disadvantages of an insufficient mechanical stability, the relatively large dust content and a limited flow capability.

The object of the present invention was a process which permits the manufacture of products which no longer have the described disadvantages and accordingly which are clearly preferred during their use, namely during incorporation into the material to be flavoured or perfumed. Foodstuffs, products consumed for pleasure and drinks, pharmaceuticals, cosmetic products, hygiene products, e.g. mouth hygiene products, diapers, soaps, detergents, household products etc. stand in the foreground.

In addition, the flavorant and odorant granulates obtainable in accordance with the invention can be provided in a second step in a simple manner with a coating without switching off or modifying the rotor-granulator which is now used in accordance with the invention or without the need to transfer product. The coating also aims at an improved encapsulation of the active substances, to achieve a modification, i.e. improvement in the solubility behaviour or a planned protective action.

Roto-granulators have hitherto been employed in the production of washing agent addivites, fertilizers and pharmaceutically active substances (see the company brochure GRCG Type 1-200 from the firm Glatt, Pratteln, Switzerland June 1992]).

The apparatus comprises essentially a fluidized bed apparatus and an arrangement for supplying and extracting air. It is conveniently e.g. a cylindrical vessel having a vertical rotating axis, the base of which rotates around the central axis. The cylinder casing is conveniently fixed. The rate of rotation is conveniently about 50–500/min. The core material provided in the process is set in motion by means of a rotating base plate. A relatively small amount of air passes through the (peripheral) annular clearance between the rotating base plate and fixed vessel wall and this together with the rotational motion of the base plate sets the material present in motion, i.e. "fluidizes". In comparison to earlier technology, which produces the required motion of the material only with the aid of air, now about ⅕—about ⅓ of the air is required in order to fluidize the solid which has been provided.

SUMMARY OF THE INVENTION

The novel process is characterized by spraying a flavorant or odorant emulsion into a core material fluidized in a fluidized bed rotor-granulator, the emulsion being sprayed into the fluidized bed below the surface of the core material and the emulsion being granulated in this manner. The process also includes essentially the use of a fluidized bed rotor-granulator in the manufacture of spherical flavorant and odorant granulates.

The still relatively high air throughput and the relatively long reaction time—in relation to the danger of losing—especially—readily volatile components—spoke against the use of such apparatuses for flavorant or odorant compositions.

The core material is a solid usually used for the manufacture of flavorant or odorant granulates and which is industrially permitted or which is pharmaceutically usable, conveniently with particle sizes of about 0.02 to about 3.0 mm, especially of 0.2 to about 1.5 mm, diameter. It is, for example, a carbohydrate, e.g. a sugar such as glucose, lactose, sucrose, or also a product of more complex composition such as fruit powder, e.g. orange juice powder, or vegetable powder, e.g. carrot juice powder, or a sugar alcohol such as isomaltol, or pectin, hydrolyzed vegetable protein (HVP), food fibres, e.g. husks, wheat fibres, cellulose fibres, etc., or an organic or inorganic salt, e.g. a citric acid salt or sodium chloride; however, herb powder, spice powder, tea powder also come into consideration.

The carrier material for the emulsion which is sprayed in is generally selected from materials which are conventional for this purpose, it is conveniently a carbohydrate, e.g. a chemically modified starch, degraded starch (dextrin, maltodextrin); natural resin, exudate, e.g. gum arabic, plant extract such as carragenan, alginates, etc. a protein, e.g. a milk protein, or gelatine, etc. or a combination of such substances.

Water or water/ethanol mixtures can be used, for example, as the solvent for the emulsion.

DETAILED DESCRIPTION OF THE INVENTION

In the granulation there can also be used usual additives such as artificial sweeteners, food dyes, vitamins, antioxidants, anti-foam agents, carbonic acid generators such as tartaric acid, acids used as condiments such as citric acid, or additional flavorants, etc., which can be added to the core material or to the spray emulsion.

The particles can be coated after the granulation, e.g. by spraying, e.g. a solution, emulsion or melt of a substance or a substance mixture which is known to be suitable for this purpose and which forms a protective skin or a protective film, such as e.g. a fat or modified cellulose, gelatine, plant or animal extract, exudate, e.g. gum arabic, degraded starch or chemically modified starch, pharmaceutically usable synthetic material, e.g. polyvinylpyrrolidone, polyethylene glycol, etc.

The suitable air temperatures are elevated temperatures, e.g. about 30° C., or 40°—about 80° C., preferably about 40°, or 50—about 70° C.

All conventional flavorants and odorants come into consideration, namely e.g of the meat, cheese, fruit, e.g. citrus, berry, tobacco, flowers, wood, spice, amber, etc. type, which can be used industrially. As flavorant and odorant components there come into consideration all components hitherto usually used for flavorant and odorant (granulates), i.e. individual components such as, e.g. menthol or vanillin, etc. or ethereal oils or fractions or mixtures of flavorant and odorant compositions. The individual components can be of natural (vegetable or animal) or synthetic origin.

The narrow particle size distribution is essentially achieved by the combined effects of the parameters: particle size of the carrier material, composition of the emulsion, spray rate of the emulsion (about 30—about 80 g/min., [e.g. in the case of the apparatus of Example 1] or 3–8 g/min*kg (total batch), structure of the rotating base plate—e.g.

smooth, nubbled or grooved, rate of rotation of the rotating base plate, air inlet velocity, air temperature (about 20—about 80° C.). This influencing by the manner in which the granulation is carried out will be well-known to a person skilled in the art and the narrow distribution can be determined by experimentation. As mentioned earlier, in the case of the present invention it leads to especially favourable values.

Under "a substantially dust-free product" there is to be understood in the present case a granulate which has a fine content (essentially core material and carrier material) which lies below 5%, this in the case of particle sizes of <0.1 mm.

An essentially spherical granulate obtainable in accordance with the invention is illustrated in FIG. 1.

EXAMPLE 1

Lemon Granulate 2.975 kg of coarse sugar and 2.975 kg of powdered sugar are placed in a rotor-granulator (type GPCG-5, firm Glatt, Pratteln).

800 g of water are placed at room temperature in a separate vessel, thereafter 595 g of maltodextrin and 105 g of chemically modified starch (dextrin) are added and dissolved therein. 350 g of lemon flavour (almost exclusively lemon oil) are slowly added while stirring vigorously (18500 rpm) with a turbine mixer of the Polytron type from the firm Kinematika, Littau. The mixture is homogenized further for 3 minutes until a stable spray emulsion is obtained. The rotor-granulator is started and the spray emulsion (70 g/min.) is pumped in through a binary nozzle (emulsion/compressed air) at about half way up the fluidized bed. After the spray emulsion has been applied the flavorant granulate is dried for 5–10 minutes. There is thus obtained a free-flowing flavorant granulate having a particle size distribution of 87% within 0.2–1.0 mm and a bulk density of 0.65 g/ml.

EXAMPLE 2

Lime Granulate 4.662 kg of isomaltol are provided as the core material.

The spray emulsion is prepared as in Example 1 and consists of 2 l of water, 1.260 kg of gum arabic, 26.6 g of tartrazine (yellow colour), 1.4 g of indigotin (blue colour) and 1.050 kg of lime flavour (almost exclusively lime oil). The core material is set in motion (350 r/min.) or, respectively, fluidized and the spray emulsion is sprayed in at 75 g/min. There is obtained a flavorant granulate having 87% of the particles between 0.2 and 0.8 mm and a bulk density of 0.71 g/ml.

EXAMPLE 3

Spice Granulate

The receiver is composed of 1.680 kg of sodium chloride, 1.680 kg of crystalline sugar and 2.380 kg of HVP powder (hydrolyzed vegetable protein).

The spray emulsion is prepared as in Example 1 and contains 1 l of water, 679.7 g of maltodextrin, 210 g of modified starch and 370.3 g of a spice flavorant composition (based on lemongrass oil+pepper oleoresin). The receiver is mixed and set in motion by starting the rotor-granulator (300 r/min.). The spray emulsion is sprayed in (30 g/min.). As soon as granulation has finished and the granulate is dry, 350 g of a molten vegetable fat having a temperature of 50–60° C. is sprayed in. The temperature in the granulator is below 40° C. at this point in time, whereby the fat solidifies on the surface of the granulate. There is thus obtained a coated granulate having a spicy flavour.

EXAMPLE 4

Fruit Flavour

In this case 2.450 kg of coarse sugar and 3.500 kg of a multi-vitamin preparation (Hoffmann-La Roche, Basle) are placed in a rotor-granulator. The spray emulsion is composed of 1 l of water, 595 g of maltodextrin, 105 g of modified starch and 350 g of fruit flavour and is prepared analogously to Example 1. The granulator is operated as in Example 1, the spray emulsion is dosed in at 50 g/min.

EXAMPLE 5

Perfumed Granulate 5.250 kg of maltodextrin are placed in a rotor-granulator.

The spray emulsion is prepared as in Examples 1 to 4. It consists of 1.500 kg of water, 0.875 kg of maltodextrin, 0.175 kg of chemically modified starch and 0.700 kg of an arbitrary mixture of odorants for perfumery purposes.

The core material is set in motion (400 r/min.) or fluidized and the spray emulsion is sprayed in at 85 g/min. There is obtained a perfume granulate which is coated with 0.350 kg of polyglycol 6000 S, dissolved in 0.350 kg of ethanol, and 0.175 kg of water. The water and the ethanol evaporate and the polyglycol forms a film on the odorant granulate.

The parameters of the apparatus given in the scope of the present invention relate in each case to the rotor granulator GPCG-5 which is suitable for laboratory operation and which has a diameter of 50 cm and a height of 1.9 m (fluidized bed 92 cm); deviations are possible in the case of larger apparatuses.

The flavorant and odorant granulates mentioned in Examples 1 to 5 are utilized in foodstuffs to be flavoured such as e.g. tea powder, spice mixtures, chewing gum, frozen ready meals, soft and hard sweets, biscuits, ice cream, ice cream coating, chocolate bars, instant drink powders, packaged soups and sauces, mouth hygiene products such as denture cleaning tablets and toothpastes, etc. or used in cosmetic, hygiene, pharmaceutical, soap, detergent or household products to be perfumed.

EXAMPLE 6

Applications of the Granulates in Accordance with the Invention

Tea Bags

2–12% of granulated flavorant, e.g. lime, is mixed with crushed tea leaves and packaged in tea bags.

The advantages over conventional powder flavorants are the following:

The granulate, because of the particle size, does not pass through the pores in the paper→no loss during transport and storage.

No abrasion of the granulate particles during processing and transport, since they are mechanically resistant.

The flavorant dissolves rapidly and completely when the tea bag is immersed in hot water.

Instant Drink Powder

1–2% of a granulated flavorant, e.g. tropical fruit mix, is mixed with and instant sugar-based drink powder.

The advantages over conventional powder flavorants are especially:

No de-mixing during packaging and transport, since the granulate particle size is adjusted to the particle size of the drink powder.

Improved storage stability of the citrus flavorant in accordance with the invention.

Rapid dissolution of the flavorant when the drink powder is stirred in cold water.

Chewing Gum

An orange coloured granulated flavorant, e.g. peach, is incorporated to 0.5% in a chewing gum mass which already contains a liquid flavorant, e.g. lemon.

The chewing gum thereby has the following advantages which can not be achieved with conventional powder flavorants:

Attractive, well visible particles which remain stable during storage.

A dual flavouring effect, with the two flavours being perceptible separately.

A very rapid perception of the granulated flavorant after chewing for a few seconds, followed by the liquid flavorant, flavour is again newly liberated with each bite on a granulate particle.

Hard and Chewable Sweets

A brown coloured granulated flavorant, e.g. cinnamon, is admixed to 0.2–0.4% in a hard or chewable sweet mass which is flavoured with a liquid flavorant, e.g. apple.

Advantages:

Attractive, visible particles which remain stable during storage.

A dual flavouring effect, with the two flavours being perceived separately, the impression of apple strudel results in this case.

Chocolate

A cola flavorant, which contains Na bicarbonate and citric acid, is incorporated to 1–4% in a chocolate mass.

Advantage:

A tingling effect develops immediately upon eating in that carbonic acid forms under the influence of the moisture in the saliva.

Ice Cream with Chocolate Coating

1–3% of a granulated fruit flavorant, e.g. lemon, which also contains citric acid, is mixed in the chocolate mass. The chocolate is applied to the finished ice cream in the usual manner as a thin coating.

The following advantages are noticed when the ice cream is consumed:

Locally defined fruity flavour, as well as of fruit particles, in the chocolate.

The fruit impression is intensified by the citric acid, which is not possible with usual powder flavorants.

Granulated flavorants having a particle size of 0.8–2 mm give, in addition, a crispy effect when they are chewed.

Frozen Rice Dish

A spice flavorant, which contains salt and which is additionally coated with a hard fat layer (Example 3), is mixed with or sprinkled over boiled, cooled rice.

Advantage:

Since the salt is enclosed in the particles, it does not dissolve out and does not cause any changes when the rice dish is processed by freezing.

BRIEF DESCRIPTION OF FIGURE

Legends to FIG. 1
1) Particle structure
2) Nucleus, core (carrier material, mainly carbohydrate)
3) Encapsulated flavorant (flavorant is enclosed in a film-forming agent)
4) Coating, skin (optional, e.g. of fat, protein, carbohydrate or mixtures thereof).

Figure 1:
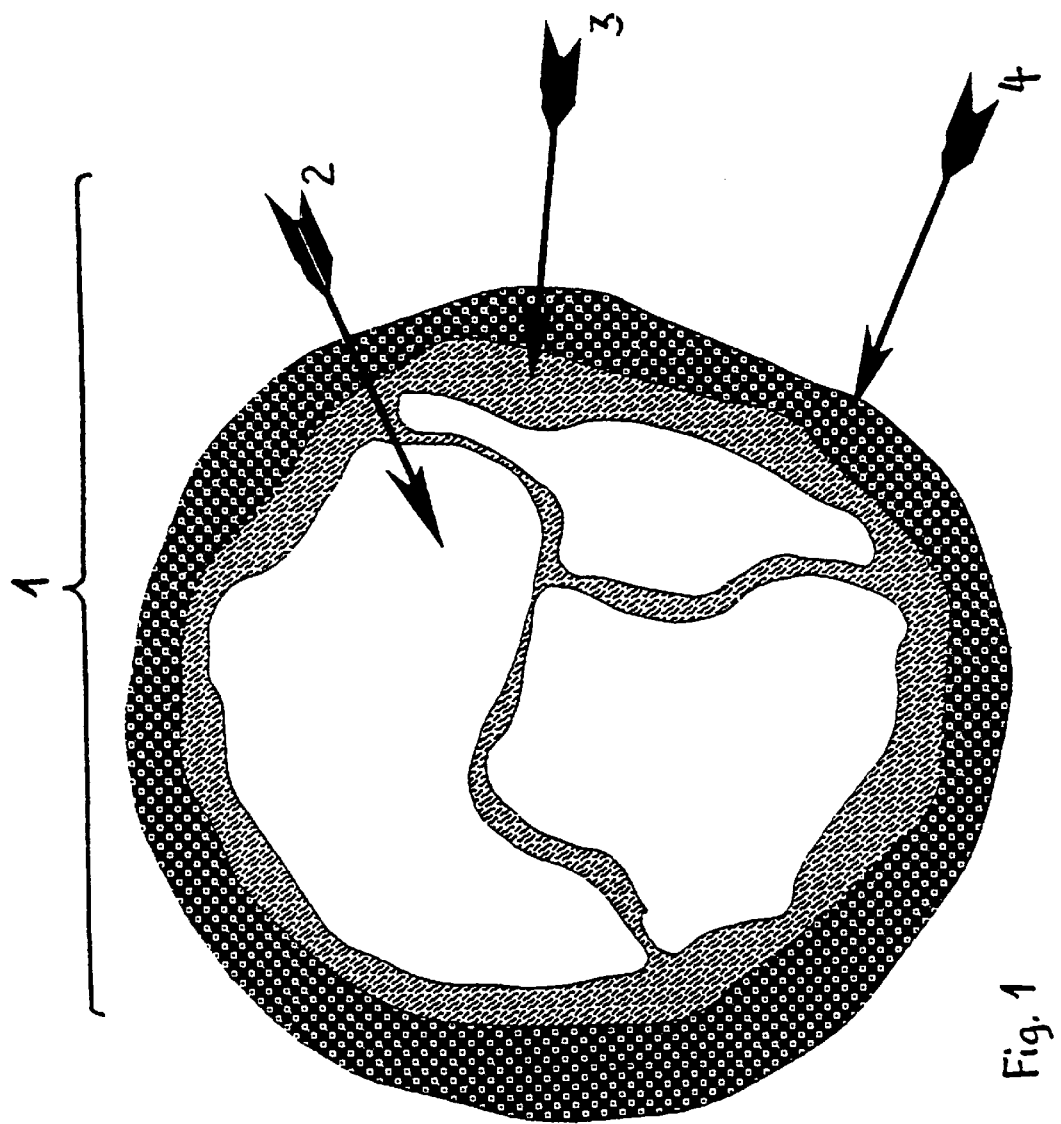

What is claimed is:

1. A process for making a spherical flavorant or odorant granulate comprising
   (a) fluidizing a core material in an air fluidized bed rotor-granulator by introducing air into the rotor-granulator to cause the material to be fluidized by air and the rotor;
   (b) spraying a flavorant or odorant emulsion below the surface of the fluidized core material; and
   (c) granulating the flavorant or odorant emulsion in the fluidized core material.

2. The process of claim 1, wherein the core material is a solid which is permitted in the foodstuff, cosmetic, pharmaceutical or consumer goods industry having a particle size of from about 0.02 mm to about 3.0 mm.

3. The process of claim 2, wherein the core material is selected from carbohydrate, a fruit powder, a vegetable powder, a sugar alcohol, hydrolyzed vegetable protein, food fibers, an organic or inorganic salt, herb powder, spice powder, tea powder or combinations thereof.

4. The process of claim 3, wherein the carbohydrate is selected from glucose, lactose, sucrose, starch, or degraded starch.

5. The process of claim 3, wherein the sugar alcohol is selected from isomaltol or pectin.

6. The process of claim 3, wherein the food fiber is selected from husks, wheat fibers, or cellulose fibers.

7. The process of claim 2, wherein the flavorant or odorant emulsion comprises a carrier material selected from carbohydrate, natural resin exudate, plant extract, protein, or combinations thereof which are in a water or water/alcohol mixture.

8. The process of claim 7, wherein the granulated flavorant or odorant comprises about 1 to about 25 percent of flavorant or odorant and the remainder being core material and carrier material.

9. The process of claim 8, wherein the granulated flavorant or odorant comprises about 5 to about 15 percent or flavorant or odorant and the remainder being core material and carrier material.

10. The process of claim 8, wherein the granulated flavorant comprises about 10 percent of flavorant or odorant and the remainder being core material and carrier material.

11. The process of claim 7, wherein the granulated flavorant or odorant has a particle size of from about 0.05 mm to about 3.0 mm.

12. The process of claim 11, wherein the granulated flavorant or odorant has a particle size of from about 0.2 mm to about 1.5 mm.

13. The process of claim 11, wherein $\geq 95\%$ of the particles are from about 0.2 mm to about 3 mm in diameter.

14. The process of claim 13, wherein about 80% of the particles have a diameter of about 0.6 mm.

15. The process of claim 7, wherein the granulated flavorant or odorant is further coated by a fat, modified cellulose, gelatin, plant extract, animal extract, exudate, degraded starch, chemically modified starch, pharmaceutically useable synthetic material, and mixtures thereof.

16. The process of claim 1, wherein the air is heated from about 20° C. to about 80° C.

17. The process of claim 16, wherein the air is heated from about 40° C. to about 60° C.

18. The process of claim 1, wherein additives selected from artificial sweeteners, food dyes, vitamins, antioxidants, anti-foam agents, carbonic acid generators, acids used as condiments, or combinations thereof are added to either the core material or the spray emulsion.

19. The process of claim 1 wherein air is introduced through an annular clearance between a rotating base plate and a fixed vessel wall of said rotor-granulator.

20. The process of claim 1 wherein said emulsion is sprayed about half way up the fluidized material.

21. The process of claim 19 wherein granulation is facilitated by a base plate having a surface structure selected from the group consisting of smooth, nubbled, and grooved.

22. The process of claim 1 wherein said emulsion is sprayed at a rate selected from the group consisting of about 30–80 g/min and about 3–8 g/min kg.

23. The process of claim 1 wherein said granulate has a particle size <0.01 mm and has a fine content less than 5%.

24. The process of claim 13 wherein said particle size distribution is achieved by controlling carrier material particle size, emulsion composition, emulsion spray rate, rotating base plate structure, rotating base plate rate of rotation, air inlet velocity, and air temperature.

* * * * *